(12) United States Patent
Dehler et al.

(10) Patent No.: US 7,887,236 B2
(45) Date of Patent: Feb. 15, 2011

(54) X-RAY SOURCE FOR A MOBILE X-RAY DIAGNOSTIC UNIT WITH A C-ARM

(75) Inventors: Juergen Dehler, Forchheim (DE); Michael Guenther, Nuremberg (DE); Klaus Hoerndler, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 0 days.

(21) Appl. No.: 12/134,633

(22) Filed: Jun. 6, 2008

(65) Prior Publication Data

US 2008/0304625 A1    Dec. 11, 2008

(30) Foreign Application Priority Data

Jun. 8, 2007    (DE) ................ 10 2007 026 677

(51) Int. Cl.
*H05G 1/10* (2006.01)
*H05G 1/06* (2006.01)
*H05G 1/02* (2006.01)
*H01J 35/02* (2006.01)

(52) U.S. Cl. ............... 378/197; 378/198; 378/130; 378/101

(58) Field of Classification Search ............... 378/4–20, 378/91, 98.8, 101, 102, 193, 197, 198, 130, 378/141, 144
See application file for complete search history.

(56) References Cited

U.S. PATENT DOCUMENTS

| | | | | |
|---|---|---|---|---|
| 3,281,598 A * | 10/1966 | Hollstein | ................ | 378/179 |
| 4,264,818 A * | 4/1981 | Petersen | ................ | 378/141 |
| 4,375,105 A * | 2/1983 | Baumann | ................ | 378/92 |
| 4,768,216 A * | 8/1988 | Harvey et al. | ................ | 378/110 |
| 4,856,036 A * | 8/1989 | Malcolm et al. | ................ | 378/116 |
| 4,955,046 A * | 9/1990 | Siczek et al. | ................ | 378/197 |
| 4,979,198 A * | 12/1990 | Malcolm et al. | ................ | 378/102 |
| 5,091,929 A | 2/1992 | Grady | | |
| 6,364,526 B2 | 4/2002 | Ivan et al. | | |
| 6,418,191 B1 * | 7/2002 | Fehre et al. | ................ | 378/105 |
| 6,609,826 B1 * | 8/2003 | Fujii et al. | ................ | 378/198 |
| 6,814,488 B2 * | 11/2004 | Thandiackal et al. | ........ | 378/194 |

(Continued)

FOREIGN PATENT DOCUMENTS

DE        37 82 088      4/1993

(Continued)

OTHER PUBLICATIONS

Examiner's Report, dated Dec. 4, 2009, filed in DE 10 2007 026 677.6, 3 pg.

*Primary Examiner*—Edward J Glick
*Assistant Examiner*—Anastasia Midkiff
(74) *Attorney, Agent, or Firm*—Knobbe, Martens, Olson & Bear LLP

(57) ABSTRACT

Embodiments of an X-ray source for a mobile X-ray diagnostic unit with a C-arm include a generator vessel that may be mounted to a hollow frame of the C-arm. The generator vessel may have a first subregion with a high-voltage generator and a second subregion with an X-ray source. In some embodiments, the first subregion, the second subregion, or both subregions may be at least partially inside a portion of the hollow frame of the C-arm. The generator vessel may be at least partially filled with insulating oil for cooling the high-voltage generator and/or the X-ray source.

20 Claims, 2 Drawing Sheets

U.S. PATENT DOCUMENTS

| | | |
|---|---|---|
| 6,880,691 B2 | 4/2005 | Simmons |
| 7,826,592 B2 * | 11/2010 | Jaffray et al. ................. 378/65 |
| 2002/0003854 A1 * | 1/2002 | Ivan et al. ..................... 378/20 |
| 2002/0146092 A1 * | 10/2002 | Richardson et al. ......... 378/130 |
| 2002/0154742 A1 | 10/2002 | Feldman |
| 2007/0140430 A1 * | 6/2007 | Horndler et al. ............ 378/130 |
| 2008/0198968 A1 * | 8/2008 | Takekoshi et al. ............ 378/62 |
| 2008/0221479 A1 * | 9/2008 | Ritchie et al. ............... 600/563 |
| 2009/0010386 A1 * | 1/2009 | Peschmann .................. 378/57 |

FOREIGN PATENT DOCUMENTS

| | | |
|---|---|---|
| DE | 44 23 359 | 1/1996 |
| DE | 196 30 888 | 2/1998 |
| DE | 298 02 014 | 6/1998 |
| DE | 198 24 008 | 12/1999 |
| DE | 10 2007 026 677.6 | 12/2008 |
| EP | 0 488 991 | 6/1992 |
| EP | 2 016 901 | 1/2009 |
| FR | 2 342 704 | 9/1977 |
| FR | 2 671 507 | 7/1992 |
| GB | 351 534 | 3/1930 |

\* cited by examiner

X-RAY SOURCE FOR A MOBILE X-RAY DIAGNOSTIC UNIT WITH A C-ARM

CROSS-REFERENCE TO RELATED APPLICATIONS

This application claims the right of priority under 35 U.S.C. §119(a)-(d) to German Patent Application No. DE 10 2007 026 677.6, filed Jun. 8, 2007, the entire disclosure of which is hereby incorporated by reference herein and made part of this specification.

BACKGROUND

1. Field

The disclosure relates generally to X-ray diagnostic units and more particularly to an X-ray source for a mobile X-ray diagnostic unit with a C-arm.

2. Description of the Related Art

Various types of mobile X-ray diagnostic units are known. For example, German Patent No. DE 44 23 359 owned by the assignee of the present application describes an X-ray diagnostic unit with a C-arm that can be adjusted in multiple ways. An X-ray source and an X-ray receiver are arranged at opposite ends of the C-arm. In some embodiments of this unit, some or all of the adjustment axes are equipped with incremental encoders. Such an X-ray diagnostic unit advantageously allows the recording of 2-D X-ray projection images with known projection geometry, from which a 3-D X-ray model can be reconstructed.

Some X-ray diagnostic units suffer from disadvantages. For example, the angular range of movement of the C-arm along its periphery (orbital motion) may be less than 180° in some implementations (e.g., roughly 130°). In some mobile X-ray diagnostic units, if the angular range for the orbital motion were increased to 180° with otherwise equal dimensions of the C-arm, then the opening width between the X-ray source and the X-ray receiver would be reduced. This could, in some cases, substantially reduce the positioning ability of the diagnostic unit. Although the diameter of the C-arm may be increased to increase the opening width, this arrangement generally is not preferred for mobile equipment because of the corresponding increase in weight and decrease in mechanical stability due to the larger C-arm.

Various arrangements for X-ray diagnostic units are known. For example, X-ray diagnostic units with C-arms in which the X-ray source and the X-ray receiver are arranged inside the C-arm are described in U.S. Pat. No. 6,880,691 and French laid-open application FR 2 671 507 A.

U.S. Pat. No. 6,364,526 and French laid-open application FR 2 342 704 A describe X-ray diagnostic units in which the X-ray receiver and the X-ray source are located on a side of the C-arm. The X-ray receiver and source can be displaced outward from the center point of the C-arm sufficiently that the opening width is not impaired by these components. The disclosed asymmetrical arrangement of these diagnostic units is disadvantageous, because the lateral extent of the C-arm with the X-ray source is enlarged and the positioning ability is impaired, especially for under-the-table uses.

United Kingdom Patent GB 351,534 A describes an example of a mobile X-ray source in which an X-ray tube, preferably in an insulating oil container, is connected via a high voltage cable to a high-voltage generator. The high-voltage cable is not very flexible, particularly for voltages in the range of about 80 kV, and is difficult to accommodate given the constricted space conditions in the interior of a mobile X-ray diagnostic unit.

A compact X-ray radiator for a mobile X-ray diagnostic unit is disclosed in German Patent DE 198 24 008 C2. The diagnostic unit has an X-ray tube and a high-voltage generator in an oil-filled vessel, which is arranged at one end of the C-arm and outside the area of the guide rails in the circumferential direction.

German Utility Model No. DE 298 02 014 U1 discloses a mobile X-ray diagnostic unit with a C-arm that has an X-ray radiator at one end, with the available space of the C-frame used for running the cables.

SUMMARY

Because of the foregoing (and other) challenges and limitations, the applicants have recognized there is a need for a mobile X-ray diagnostic unit with a C-arm in which the distance of the X-ray source from the center of the C-arm is enlarged for an equal C-arm diameter. In some embodiments, the C-arm has a hollow frame and includes a generator vessel housing a compact X-ray source and a high-voltage generator. The generator vessel may be mounted to the hollow frame of the C-arm. In certain embodiments, the generator vessel may have a first subregion with the high-voltage generator and a second subregion with the X-ray source. In various embodiments, the first subregion, the second subregion, or both subregions may be at least partially inside a portion of the hollow frame of the C-arm. Insulating oil may be added to the generator vessel to cool the high-voltage generator and/or the X-ray source.

In some embodiments, an X-ray source is provided for a mobile X-ray diagnostic unit with a C-arm having a frame with a hollow portion. The X-ray source comprises a generator vessel configured to be mounted to a hollow portion of the frame of the C-arm. The generator vessel may comprise a first subregion that comprises a high-voltage generator and a second subregion that comprises an X-ray tube. In various embodiments, at least one of the first subregion and the second subregion is at least partially inside the hollow portion of the frame. In some embodiments, the generator vessel is configured to be at least partially filled with a first insulating oil for the high-voltage generator and a second insulating oil for the X-ray tube. In some embodiments, the first insulating oil and the second insulating oil are the same oil shared between the first subregion and the second subregion.

In some embodiments, the generator vessel comprises at least one cooler for the shared insulating oil. The at least one cooler may comprise two or more heat exchangers in fluid communication by fluid connectors disposed outside the generator vessel.

In some embodiments, the frame of the C-arm further comprises a U-shaped portion adjacent the hollow portion. The U-shaped portion may be configured so that the C-arm can be movably attached to a mount of the X-ray diagnostic unit. In some embodiments, the U-shaped portion comprises one or more guide rails.

In some embodiments of the X-ray source, the generator vessel comprises a first housing that comprises the first subregion and a second housing that comprises the second subregion. The first housing and the second housing may be configured to be removably attached to each other. In some embodiments, the first housing is configured to be at least partially filled with a first insulating oil, and the second housing is configured to be at least partially filled with a second insulating oil. In some embodiments, the first insulating oil and the second insulating oil are separate oils that are not shared between the first housing and the second housing. In some embodiments, the second housing comprises at least one cooler for the second insulating oil.

In some embodiments of the X-ray source, the first housing comprises at least two high-voltage electrical connections configured to pass from the first housing to the second housing. In some embodiments, the second housing comprises at least two high-voltage electrical connections configured to be detachably connected by a plug to the high-voltage electrical connections from the first housing. In some embodiments, the at least two high-voltage electrical connections from the first housing are configured to pass through an opening in a wall of the second housing. The wall of the second housing may be adjacent the first housing when the housings are attached. In some embodiments, when the first housing and the second housing are attached to each other, the opening in the wall of the second housing is sealed by a portion of a wall of the first housing, the electrical connections from the first housing, and a circumferential seal disposed between the first housing and the second housing.

In some embodiments of the X-ray source, the X-ray tube comprises a rotary anode tube having a rotation axis configured to be perpendicular to a plane of the C-arm. In some such embodiments, the first subregion may be at least partially inside the hollow portion of the frame.

Embodiments of a mobile X-ray diagnostic unit are disclosed. The X-ray diagnostic unit may comprise a movable chassis and a C-arm having a frame with a hollow portion. The frame may be mounted on the movable chassis so that the C-arm can be circumferentially adjusted. In some embodiments, the C-arm comprises an X-ray source. The X-ray source may comprise a generator vessel that is configured to be mounted to the hollow portion of the frame of the C-arm. The generator vessel may comprise a first subregion that comprises a high-voltage generator and a second subregion that comprises an X-ray tube. In various embodiments, at least one of the first subregion and the second subregion is at least partially inside the hollow portion of the frame of the C-arm. In some embodiments, the generator vessel is configured to be at least partially filled with a first insulating oil for the high-voltage generator and a second insulating oil for the X-ray tube. In some embodiments, the first insulating oil and the second insulating oil are the same oil shared between the first subregion and the second subregion. In some embodiments, the generator vessel comprises a first housing that comprises the first subregion and a second housing that comprises the second subregion. The first housing and the second housing may be configured to be removably attached to each other.

BRIEF DESCRIPTION OF THE DRAWINGS

The following drawings and the associated descriptions are provided to illustrate embodiments of the present disclosure and do not limit the scope of the claims.

FIGS. 2b, 2d, 2f, 2h, 2j, and 2l are cross section views from the side of the C-arm, and FIGS. 2c, 2e, 2g, 2i, 2k, and 2m are corresponding plan views.

DETAILED DESCRIPTION OF PREFERRED EMBODIMENTS

Figure 1:
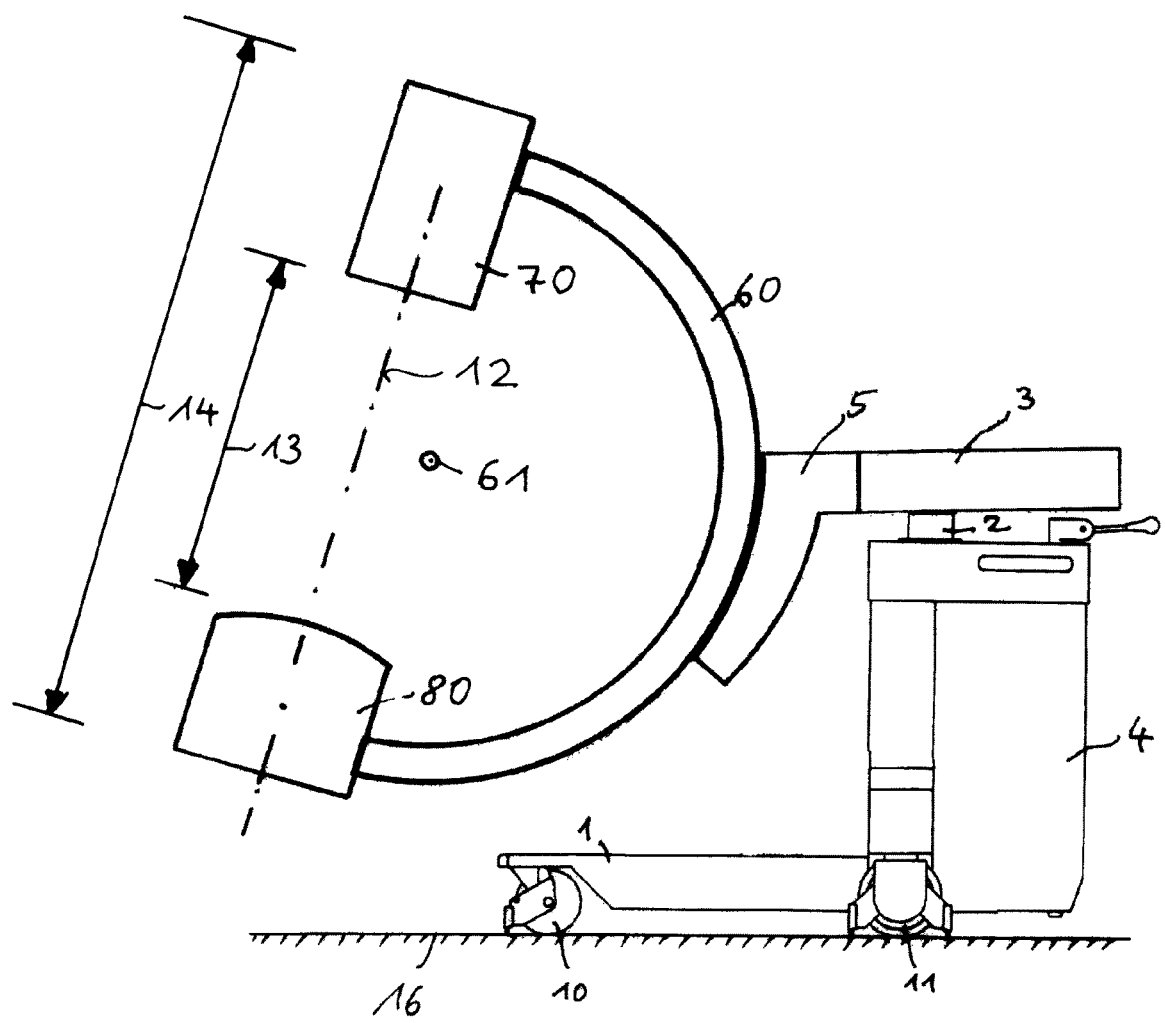
FIG. 1 schematically illustrates an embodiment of a mobile X-ray diagnostic unit having a C-arm.

FIG. 1 schematically illustrates an embodiment of a mobile X-ray diagnostic unit having an arc-shaped C-arm 60. The illustrated embodiment of the C-arm 60 approximately forms a portion of a circle having a center point 61. The C-arm 60 is movably mounted along its periphery on a mount 5, which is connected to a horizontal guide 3 and a vertical column 2. The vertical column 2 is connected to a movable chassis 1, which includes an equipment cabinet 4. The movable chassis 1 has rollers 10, 11 that allow the X-ray diagnostic unit to be moved on the floor 16. The C-arm 60 may be adjusted vertically and horizontally by adjusting the column 2 and the guide 3, respectively. The C-arm 60 may be adjusted orbitally by circumferentially moving the C-arm 60 relative to the mount 5.

In some embodiments of the C-arm 60, an X-ray source 80 is positioned at one end of the C-arm 60, and an X-ray receiver 70 is positioned at the opposite end. X-rays may propagate from the X-ray source 80 to the X-ray receiver 70 along a beam 12. The X-ray diagnostic unit shown in FIG. 1 has an opening width 13 and an outside diameter 14. In certain implementations, good positioning ability may be provided by configuring the X-ray diagnostic unit so that the opening width 13 is as large as practical and/or the outside diameter 14 is as small as practical. In certain such implementations, this may be achieved, for example, if the X-ray receiver 70 comprises a solid-state imaging detector (e.g., a flat-panel detector, FPD) and/or if the X-ray source 80 is modified as described herein.

Figure 2:
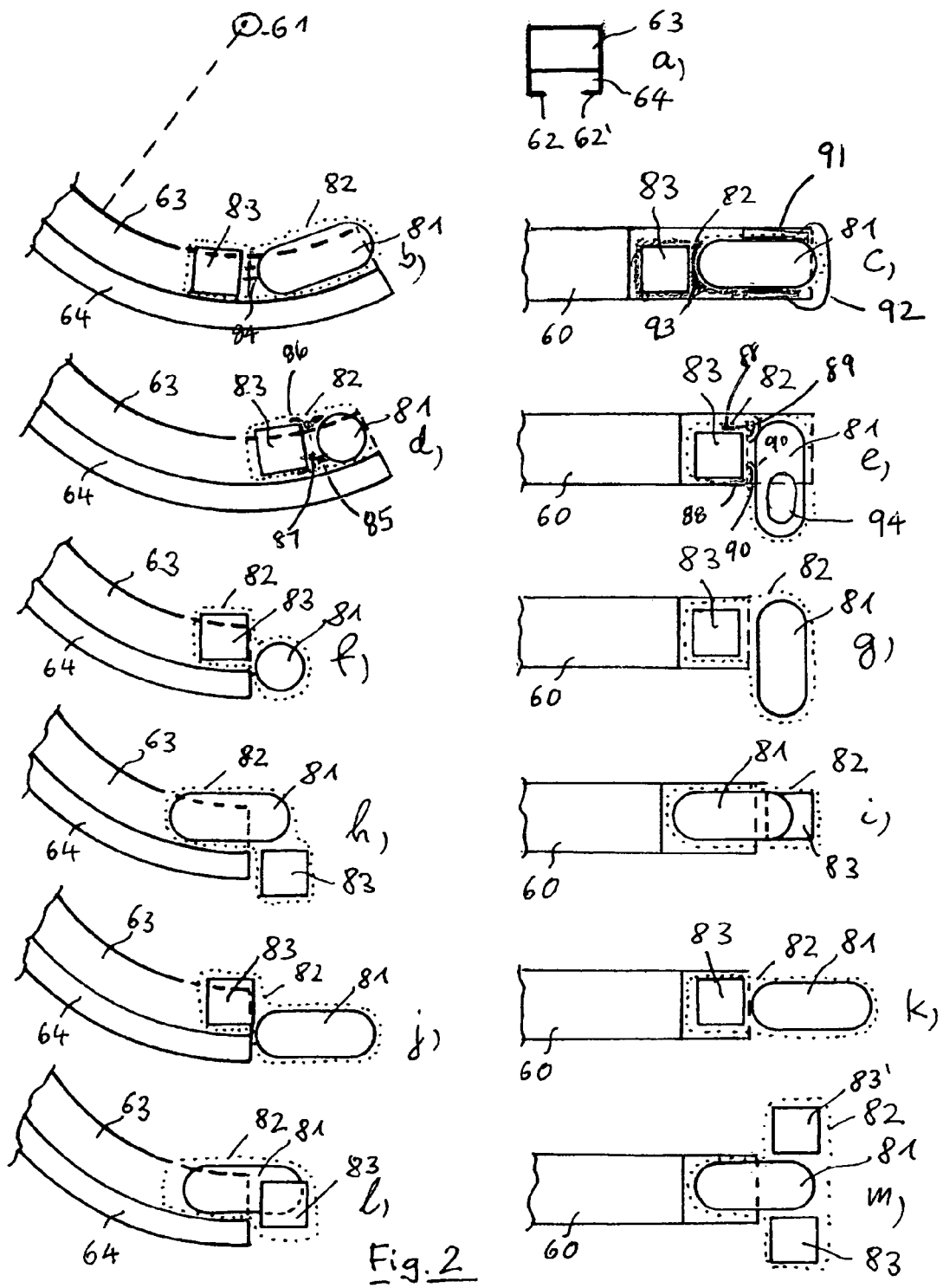
FIG. 2a schematically illustrates a cross-section view of an embodiment of a C-arm for a mobile X-ray diagnostic unit. The cross-section is taken along the arc of the C-arm.
FIGS. 2b-2m schematically illustrate examples of end portions of C-arm embodiments. The end portions include a generator vessel schematically represented as a dotted line.

FIG. 2a schematically illustrates a cross-section view of an embodiment of a C-arm 60 for a mobile X-ray diagnostic unit. The cross-section is taken along the arc of the C-arm 60. The C-arm 60 has a hollow frame 63 that is attached or adjacent to a substantially U-shaped frame 64 having guide rails 62, 62'. The guide rails 62, 62' may be used to movably mount the C-arm (60) on the mount 5. Additional examples of frames 63, 64 for C-arms 60 are described in German Patent DE 196 30 888 A1.

FIGS. 2b-2m schematically illustrate examples of end portions of C-arm embodiments. The end portions include a generator vessel 82 schematically represented as a dotted line. FIGS. 2b, 2d, 2f, 2h, 2j, and 2l are cross section views from the side of the C-arm, and FIGS. 2c, 2e, 2g, 2i, 2k, and 2m are corresponding plan views.

The generator vessel 82 comprises an X-ray source 81 and a high-voltage generator 83. The X-ray source 81 may comprise an X-ray tube. In the schematic illustrations shown in FIGS. 2b-2m, a covering of the X-ray source 81 is not shown. In some embodiments, the generator vessel 82 may comprise two or more high-voltage generators 83, 83' (see, e.g., FIG. 2m). The generator vessel 82 may be at least partially filled with insulating oil. The high-voltage generator 83 may provide electrical power to the X-ray source 81 via electrical connections (which are not shown in FIGS. 2b-2m). In some embodiments, electrical, optical, and/or hydraulic connection lines (not shown in FIGS. 2b-2m) may connect the generator vessel 82 and the equipment cabinet 4 of the X-ray diagnostic unit. In some embodiments, components for supporting convection and/or for removing waste heat generated by operation of the high-voltage generator 83 and the X-ray source 81 may be disposed in the generator vessel 82.

Embodiments of the generator vessel 82 can be welded from sheet-metal or can be constructed as a pressure-cast component made from a light metal alloy. In some cases, the generator vessel 82 is formed as a low-molded component from composite materials.

In certain embodiments, the generator vessel 82 comprises a first subregion and a second subregion. The first subregion can include the high-voltage generator 83, and the second subregion can include the X-ray source 81. In some embodiments, the first and the second subregions include insulating oil 93 that at least partially fills the generator vessel 82. The first subregion and the second subregion may be interconnected, and in some case, the insulating oil may be shared between the two subregions. In various embodiments, one or both of the two subregions of the generator vessel 82 may be configured to be at least partially inside the hollow frame 63 of the C-arm 60 (see FIGS. 2*b*-2*m*).

As shown in the embodiments depicted in FIGS. 2*b*-2*e*, the first and the second subregions of the generator vessel 82 can be arranged so that they are both at least partially inside the hollow frame 63 of the C-arm 60. In other embodiments, only one of the subregions is at least partially inside the hollow frame 63. For example, in the embodiments shown in FIGS. 2*f*-2*g* and 2*j*-2*k*, the first subregion (with the high-voltage generator 83) is at least partially in the hollow frame 63. In the embodiments shown in FIGS. 2*h*-2*i* and 2*l*-2*m*, the second subregion (with the X-ray source 81) is at least partially in the hollow frame 63.

In some embodiments, portions of the walls of the hollow frame 63 that face toward the center point 61 of the C-arm 60 may be removed in the area of the generator vessel 82 (locations of removed portions are indicated as heavy dashed lines in the cross-sections shown in FIGS. 2*b*, 2*d*, 2*f*, 2*h*, 2*j*, and 2*l*). In some embodiments, if additional space is desired, portions of the lateral walls may be removed. In certain embodiments, if the stability or structural integrity of the C-arm 60 is reduced by removing portions of the hollow frame 63 in the area of generator vessel 82, then the C-arm 60 may be reinforced in this area.

In certain embodiments, the generator vessel 82 is formed from two housings that are detachable from each other. The first housing may comprise the first subregion, and the second housing may comprise the second subregion. In certain embodiments, the first housing includes the high-voltage generator 83 and the second housing includes the X-ray source 81. Each housing may have its own separate insulating oil that is not shared with the other housing. In some embodiments, there are at least two high-voltage electrical connections 84 that pass through a portion of the vessel wall that separates the first housing and the second housing. In some embodiments, there are at least two high-voltage electrical connections 85 in the second housing of the generator vessel 82 that may be detachably and electrically connected by a plug 87 to the two high-voltage electrical connections 86 from the first housing. An advantage of certain such embodiments is that if the X-ray source 81 needs to be exchanged (e.g., in a service situation), the second housing of the generator vessel 82 can be detached from the first housing, without having to change the sealing of the insulating oil.

In some arrangements, the first housing of the generator vessel 82 includes at least two high-voltage electrical connections 88, and the second housing (with the X-ray source 81) includes at least one opening 89 on the side of the wall facing the first housing. The at least one opening may be positioned to receive the high-voltage electrical connections. In some embodiments, the at least one opening in the wall of the second housing is sealed by the wall of the first housing, by the high-voltage electrical connections, and/or by a seal 90 arranged circumferentially between the first and the second housing. In some implementations (e.g., when service is being performed), the X-ray source 81 can be connected to the high-voltage electrical connections, and the second housing subsequently filled with insulating oil.

In certain embodiments, the generator vessel 82 may include one or more coolers 91 for cooling the insulating oil. For example, a cooler may comprise a heat exchanger. In certain such embodiments, the second housing of the vessel 82 (with the X-ray source 81) includes at least one cooler. In embodiments in which more than one cooler is utilized, it may be advantageous to interconnect the coolers outside the walls of the generator vessel 82 in order to provide parallel and/or series connections among the coolers.

In some embodiments, the X-ray source 81 may comprise a rotary anode tube, which rotates during operation and has angular momentum due to the rotation. If the C-arm 60 or the diagnostic unit is moved such that there is a change in the direction of the angular momentum vector in the Earth's gravitational field, then a force may act that is perpendicular to the axis of rotation of the rotary anode tube. Some X-ray diagnostic units may be configured to scan a patient, and in certain embodiments the scanning may utilize orbital movement of the C-arm 60. In certain such embodiments, rapid scanning may require rapid orbital movements. In some implementations, rapid orbital movements may cause changes in the X-ray projection geometry that would be less likely to occur if the C-arm 60 were moved less rapidly or quasi-statically. Accordingly, in some implementations of X-ray diagnostic units configured for rapid scanning, it may be advantageous if the X-ray source 81 is arranged as shown in FIGS. 2*d*-2*g*, and the orientation of the rotation axis of the rotary anode is arranged to be substantially perpendicular to the plane of the C-arm 60.

Although described herein in the context of a mobile X-ray diagnostic unit, a person of ordinary skill will recognize that embodiments disclosed herein may be used with other types of medical devices (e.g., magnetic resonance imaging, computerized tomography, etc.). The structures, components, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Reference throughout this specification to "some embodiments" or "an embodiment" (and the like) means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner in one or more embodiments, as would be apparent to one of ordinary skill in the art from this disclosure. Additionally, although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. An X-ray source for a mobile X-ray diagnostic unit with a C-arm having a frame with a hollow portion, the X-ray source comprising:
   a C-arm frame having a hollow portion;
   a generator vessel configured to be mounted to the hollow portion of the frame of the C-arm, the generator vessel comprising a first subregion that comprises a high-voltage generator and a second subregion that comprises an X-ray tube,
   wherein one of the first subregion and the second subregion is inside the hollow portion of the frame, and one of the first subregion and the second subregion is outside the hollow portion of the C-arm frame.

2. The X-ray source of claim 1, wherein the generator vessel is configured to be at least partially filled with a first insulating oil for the high-voltage generator and a second insulating oil for the X-ray tube.

3. The X-ray source of claim 2, wherein the first insulating oil and the second insulating oil are the same oil shared between the first subregion and the second subregion.

4. The X-ray source of claim 3, wherein the generator vessel comprises at least one cooler for the shared insulating oil.

5. The X-ray source of claim 4, wherein the at least one cooler comprises two or more heat exchangers in fluid communication by fluid connectors disposed outside the generator vessel.

6. The X-ray source of claim 1, wherein the frame of the C-arm further comprises a U-shaped portion adjacent the hollow portion, the U-shaped portion configured so that the C-arm is movably attached to a mount of the X-ray diagnostic unit.

7. The X-ray source of claim 6, wherein the U-shaped portion comprises one or more guide rails.

8. The X-ray source of claim 1, wherein the generator vessel comprises a first housing comprising the first subregion and a second housing comprising the second subregion, the first housing and the second housing configured to be removably attached to each other.

9. The X-ray source of claim 8, wherein the first housing is configured to be at least partially filled with a first insulating oil, the second housing is configured to be at least partially filled with a second insulating oil.

10. The X-ray source of claim 9, wherein the first insulating oil and the second insulating oil are separate oils that are not shared between the first housing and the second housing.

11. The X-ray source of claim 9, wherein the second housing comprises at least one cooler for the second insulating oil.

12. The X-ray source of claim 8, wherein the first housing comprises at least two high-voltage electrical connections configured to pass from the first housing to the second housing.

13. The X-ray source of claim 12, wherein the second housing comprises at least two high-voltage electrical connections configured to be detachably connected by a plug to the high-voltage electrical connections from the first housing.

14. The X-ray source of claim 12, wherein the at least two high-voltage electrical connections from the first housing are configured to pass through an opening in a wall of the second housing, the wall of the second housing adjacent the first housing when the housings are attached.

15. The X-ray source of claim 14, wherein when the first housing and the second housing are attached to each other, the opening in the wall of the second housing is sealed by a portion of a wall of the first housing, the electrical connections from the first housing, and a circumferential seal disposed between the first housing and the second housing.

16. The X-ray source of claim 1, wherein the X-ray tube comprises a rotary anode tube having a rotation axis configured to be perpendicular to a plane of the C-arm, and the first subregion is at least partially inside the hollow portion of the frame.

17. A mobile X-ray diagnostic unit comprising:
    a movable chassis; and
    a C-arm having two end portions and a frame with a hollow portion, the frame mounted on the movable chassis so that the C-arm can be circumferentially adjusted, the C-arm comprising an X-ray source and an X-ray receiver that are separated by an opening, said X-ray source comprising:
        a generator vessel configured to be mounted to the hollow portion of the frame of the C-arm, the generator vessel comprising a first subregion that comprises a high-voltage generator and a second subregion that comprises an X-ray tube, wherein at least one of the first subregion and the second subregion is at least partially inside the hollow portion of the frame of the C-arm and at least one of the first subregion and the second subregion is disposed at least partially outside the hollow portion of the frame of the C-arm in a manner so as to increase the width of the opening between the X-ray source and the X-ray receiver.

18. The mobile X-ray diagnostic unit of claim 17, wherein the generator vessel is configured to be at least partially filled with a first insulating oil for the high-voltage generator and a second insulating oil for the X-ray tube.

19. The mobile X-ray diagnostic unit of claim 18, wherein the first insulating oil and the second insulating oil are the same oil shared between the first subregion and the second subregion.

20. The mobile X-ray diagnostic unit of claim 17, wherein the generator vessel comprises a first housing comprising the first subregion and a second housing comprising the second subregion, the first housing and the second housing configured to be removably attached to each other.

* * * * *